United States Patent [19]

Schulz et al.

[11] 4,326,513
[45] Apr. 27, 1982

[54] PATIENT DATA CONTROLLED RESPIRATION SYSTEM

[75] Inventors: Volker Schulz, Mainz; Stefan Kunke, Wiesbaden; Ulrich Heim, Reinfeld, all of Fed. Rep. of Germany

[73] Assignee: Drägerwerk AG, Fed. Rep. of Germany

[21] Appl. No.: 164,573

[22] Filed: Jun. 30, 1980

[30] Foreign Application Priority Data

Jul. 2, 1979 [DE] Fed. Rep. of Germany ....... 2926747

[51] Int. Cl.³ .......................................... A61M 16/00
[52] U.S. Cl. .......................... 128/203.14; 128/204.23; 128/671
[58] Field of Search .................. 128/204.21, 204.22, 128/204.23, 203.14, 671

[56] References Cited

U.S. PATENT DOCUMENTS

| | | | |
|---|---|---|---|
| 2,754,819 | 7/1956 | Kirschbaum | 128/204.23 |
| 3,957,043 | 5/1976 | Shelby | 128/203.14 |
| 4,112,938 | 9/1978 | Jeretin | 128/204.23 |
| 4,121,578 | 10/1978 | Torzala | 128/204.23 |
| 4,127,121 | 11/1978 | Westenkow et al. | 128/203.14 |
| 4,150,670 | 4/1979 | Jewett et al. | 128/204.22 |
| 4,188,946 | 2/1980 | Watson et al. | 128/204.22 |

FOREIGN PATENT DOCUMENTS

| | | | |
|---|---|---|---|
| 2728779 | 1/1978 | Fed. Rep. of Germany | 128/204.22 |
| 2744327 | 4/1978 | Fed. Rep. of Germany | 128/204.22 |
| 11600 | 9/1977 | United Kingdom | 128/204.22 |

OTHER PUBLICATIONS

Coles et al., "Computer Control of Respiration and Anesthesia", Medical and Biological Engineering, May 1973, pp. 262-267.

*Primary Examiner*—Henry J. Recla
*Attorney, Agent, or Firm*—McGlew and Tuttle

[57] ABSTRACT

A respiration system and method for minimizing the oxygen concentration of inspiration gas supplied to a patient while maintaining a desired arterial oxygen partial pressure in the patient comprising a regulator for changing the oxygen concentration of inspiration gas supplied to a respirator according to a desired nominal value therefor and a sensed value therefor taken from the patient, a control device for adjusting parameters of the breathing gas in the respirator supplied to the patient while maintaining the desired arterial oxygen partial pressure, and a minimizer connected to the control device for changing a direction of the adjustment when the oxygen concentration in the inspiration gas cannot be maintained within a range between a first sensed instantaneous value for the oxygen concentration in the inspiration gas and a lower limit set for that value.

7 Claims, 2 Drawing Figures

PATIENT DATA CONTROLLED RESPIRATION SYSTEM

FIELD AND BACKGROUND OF THE INVENTION

The present invention relates in general to respiration systems and, in particular, to a new and useful patient data controlled respiration system utilizing sensed concentrations of oxygen in the patient's blood to control a respirator supplying breathing air having a selected concentration of oxygen therein to the patient.

Patient respiration using respirators should ensure a sufficient oxygen supply to the body tissue of the patient. An optimum saturation of the blood is desired. If the oxygen or breathing gas supply is provided with an excessive inspiration $O_2$ concentration this may lead to changes in the pulmonary tissue and in the blood circulation, as well as to toxic effects, particularly with prolonged respiration. In addition, incipient insufficiencies are masked by the ample supply and prevent early diagnosis. For this reason, the oxygen concentration in the inspiration gas ($FiO_2$) should be kept as low as possible.

A known respiration system has a device for controlling and regulating a respirator. The respirator is controlled in dependence on physiological parameter of a patient and the analytical values of the gaseous components of the blood. To this end, the measured values obtained on the patient by a pulmonary function meter and analyzer, are fed to a computer and to a main control unit. The main control unit influences the composition of the gas mixture using a gas mixer of the respirator, and the other output quantities of the respirator are established by a control and regulating device. Another control unit causes a variation of the output quantities of the respirator at certain time intervals and for a short time in each interval. From the signals obtained from the patient in the course of these varations, the computer forms control signals for the main control unit. The main control unit then controls the output quantities of the respirator. Possibilities for optimizing certain values, like arterial $O_2$ partial pressure ($PaO_2$) or ($FiO_2$), do not result from this known respiration system, however. It merely determines factors which are useful for carrying out a program to be indicated below (see DOS No. 2,744,327).

SUMMARY OF THE INVENTION

The object of the present invention is to provide a respiration system which achieves maximum protection of the patient by maintaining his optimum arterial partial pressure of oxygen or $PaO_2$ by supplying the lowest possible inspiration concentration of oxygen, these termed $FiO_2$.

Accordingly, another object of the present invention is to provide a respirator system which is controlled in response to data obtained from the patient where breathing gas with a selected inspiration gas oxygen concentration is supplied to the respirator from a mixer which receives a value for the inspiration gas oxygen concentration from a regulator controlled by a desired nominal value for the arterial partial pressure of the patient and an actual value of such partial pressure supplied by a sensor connected to the patient. An instantaneous actual value for the inspiration gas oxygen concentration is supplied to a storage and to a minimizing comparator which compares the instantaneous value for the oxygen concentration with subsequent values produced by the mixer to produce a signal when the subsequent values rise above the instantaneous value or fall below a selected minimum value. A control device is connected to the minimizing comparator and a setting arrangement of the respirator for adjusting one selected parameter at a time of the respirator in one direction if no signal is produced by the minimizing comparator and in an opposite direction if a signal is produced by the minimizing comparator to minimize the inspiration gas oxygen concentration.

By adjusting the respiration parameters, the $FiO_2$ is reduced by the minimizor to a minimum value at which the $PaO_2$ is kept constant by the regulator at the desired value. This was not possible heretofore, and is of benefit to the patient. The automatic operation makes the minimization operation independently of a manual control.

Other objects of the present invention include providing a respirator system which includes a plurality of sensors for sensing different conditions of the patient with a window comparator connected to each of said sensors. Each of the window comparators and the minimizing comparator are connected to an OR-gate which in turn is connected to the control device.

A further object of the invention is to provide a warning device on each of the window comparators for indicating conditions at which the value for the inspiration gas oxygen concentration cannot be maintained between the instantaneous value therefor and the lower selected value therefor.

Another object of the present invention is to provide a respiration system including a warning device connected to the output of the minimizing comparator and a still further object of the present invention is to provide a respirator system including an alarm connected to the control device itself.

The use of additional patient data as an additional criterion for maintaining parameter variations leads to a particularly gentle treatment of the patient, because it ensures that the additional patient data will not leave certain favorable ranges in the course of the minimization of the $FiO_2$. The equipment with warning devices and an alarm also serves to protect the patient, as well as to facilitate the work of the operators by making the appearance and the type of deviations, as well as changes in the conditions of the patient which cannot be handled by the respirator, immediately recognizable. Corrections can then be made at once.

Another object of the present invention is to provide a method for minimizing the oxygen concentration of inhalation gas provided to the patient while maintaining the desired value of arterial oxygen partial pressure for the patient.

Another object of the invention is to provide a respirator system which is simple in design, rugged in construction and economical to manufacture.

The various features of novelty which characterize the invention are pointed out with particularly in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
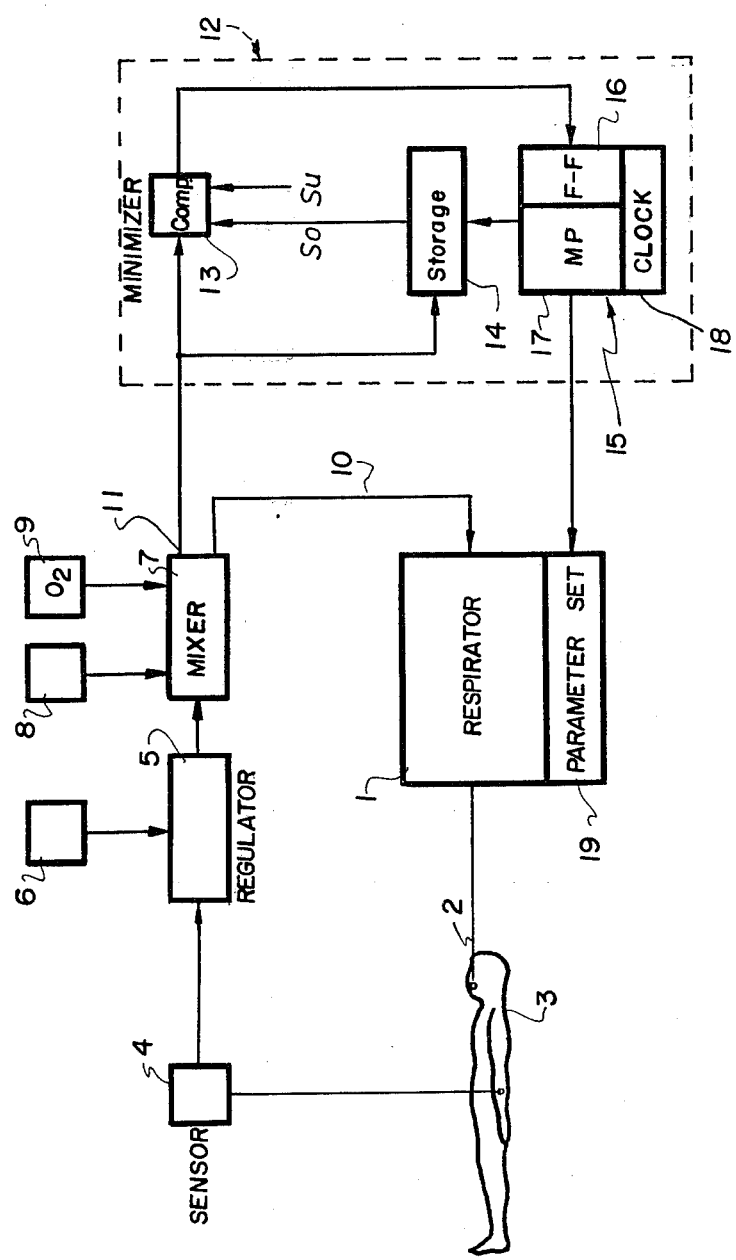
FIG. 1 is a block diagram showing the respirator system in one embodiment thereof.

Turning to the drawings in particular, the invention embodied therein, in FIG. 1 comprises a respirator system for providing breathing gas having a selected inspiration gas oxygen concentration to a patient 3 from a respirator 1 which is supplied with the breathing gas from a mixer 7. Regulator 5 controls the mixer 7 to provide sufficient oxygen concentration in the inspiration gas so that an arterial oxygen partial pressure is maintained in the patient. A plurality of parameters for the breathing gas is adjusted by a setting arrangement 19 which in turn is controlled by a control device 15 which is responsive to the attainment or non-attainment of the desired arterial oxygen partial pressure to selectively adjust the setting arrangement 19 so that the oxygen concentration of the inspiration gas is minimized while still maintaining the desired arterial oxygen partial pressure.

In FIG. 1, respirator 1 is connected to breathing gas line 2 which is connected to the lungs of a patient 3. The $PaO_2$ sensor 4 is connected, for example, to a blood vessel of patient 3 and measures his $PaO_2$. It transmits this signal to the actual value input of regulator 5. A nominal value input is provided to regulator 5 by nominal value transmitter 6. A nominal value signal is provided which corresponds to the desired $PaO_2$. The output signal of regulator 5 controls gas mixer 7. Mixer 7 is supplied by gas supplies 8 and 9 with oxygen and other gas to form a breathing gas. The breathing gas flows over connecting line 10 to repirator 1 and then over breathing gas line 2 to patient 3. Regulator 5 ensures the continuous maintenance of the desired $PaO_2$ level of patient 3 using the $FiO_2$ value of the breathing gas as determined by the regulator 5. Mixer 7 transmits, at the same time, at signal output 11, a signal corresponding to the instantaneous $FiO_2$ of the breathing gas to minimizing comparator 13 and to storage 14 of minimizer 12. Storage 14, as a threshold value transmitter for the upper threshold value So, is connected to minimizing comparator 13. The lower threshold value Su of minimizing comparator 13 is set on a threshold value transmitter (not shown). The output of minimizing comparator 13 is connected to control device 15 and device 15 is connected to storage 14 and setting arrangement 19 on respirator 1.

Control device 15 comprises a flip-flop 16, a microprocessor 17 for controlling the operations, and a master clock 18. Device 15 controls the setting arrangement 19, in a given order for the adjustment of respiration parameters of respirator 1, such as the tidal volume, breathing frequency, minute volume, chronological flow pattern, end-inspiratory pause, amplitude of the breathing gas current, end-inspiratory plateau pressure, peak pressure, PEEP pressure, apparatus dead space, apparatus compliance or inspiratory $CO_2$ concentration and the like. The respective respiration parameter is adjusted or varied by a fraction, e.g. by 1/10 of its adjustment range. Depending on the type of the respective respiration parameter, the master clock 18 is set by microprocessor 17 to provide a certain clock time period. Each clock time period is sufficiently long so that, with the adjustment of a corresponding parameter, there is enough time for the $PaO_2$ value to be effected.

The following sequence of operations takes place: Clock 18 starts the first time period. Control device 15 sets its flip-flop 16 for an output signal 0. At the same time, device 15 causes storage 14 to store the instantaneous $FiO_2$ value of mixer 7 and to feed it as signal So to minimizing comparator 13. Furthermore, device 15 causes, through setting arrangement 19, the adjustment of a selected first respiration parameter. The result is a variation of the actual $PaO_2$ value which causes a change, over regulator 5 and mixer 7, of the $FiO_2$ value to retain the desired $PaO_2$ value. If the signal of mixer 7 is determined, during the first clock time period to be between the threshold value So and Su of minimizing comparator 13, the comparator 13 gives off a 0-signal and flip-flop 16 remains at output signal 0. After the expiration of the first clock time period, the direction of the successful adjustment of the first respiration parameter is stored in microprocessor 17. This direction is used for adjustment, the next time this first parameter comes up for adjustment. The above-described process then repeats itself in the adjustment of a 2nd selected respiration parameter for a second time period where the $FiO_2$ just attained during the last time period serves as a new threshold value So for minimizing comparator 13.

Figure 2:
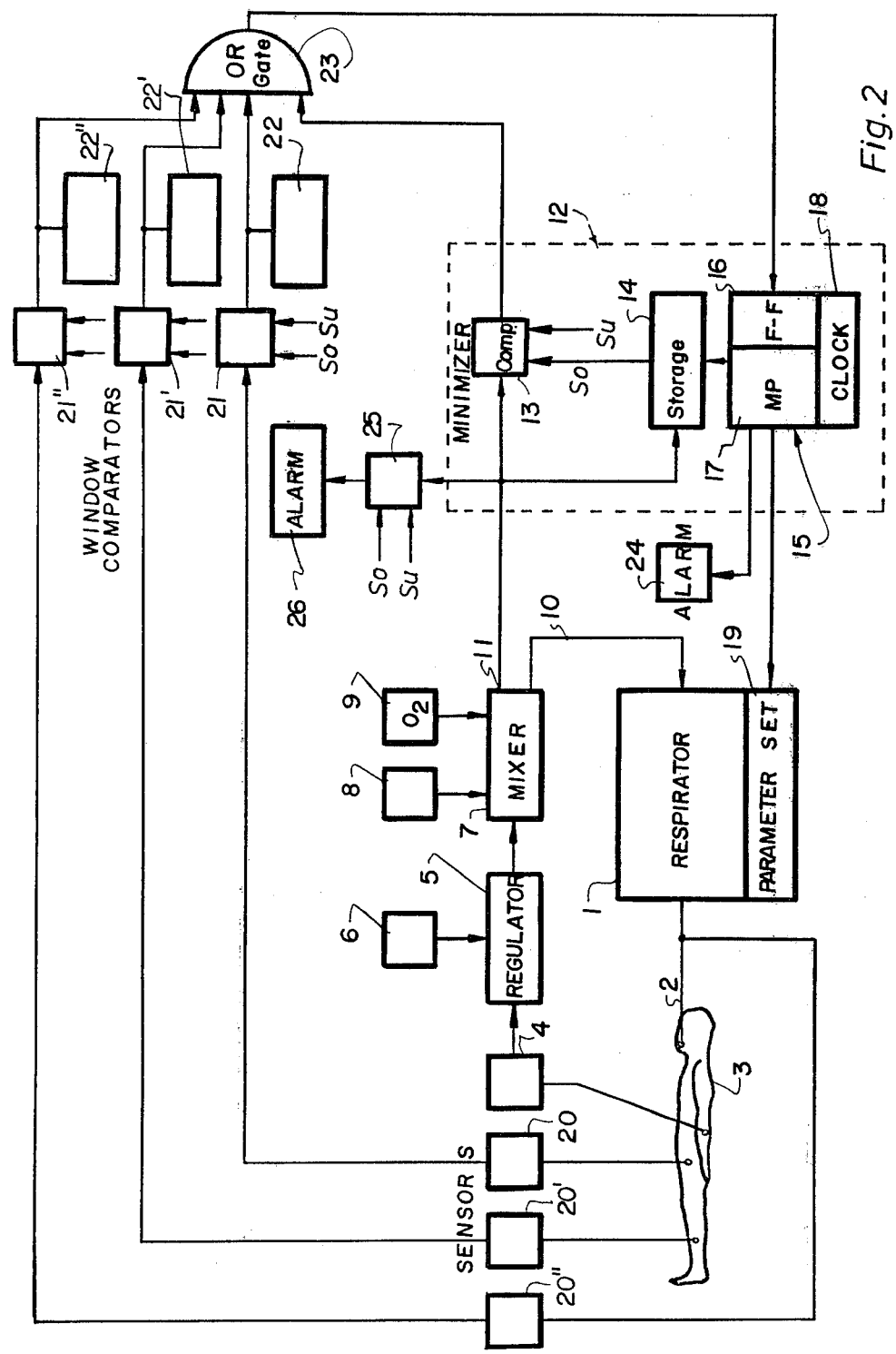
FIG. 2 is a view similar to FIG. 1 of an alternate embodiment of the invention.

If an adjustment (over 19) has the result, immediately, or within the clock time period, that the $FiO_2$ value is above So or below Su, the minimizing comparator 13 gives off a 1-signal and switches flipflop 16 to output signal 1. This also takes place when a transient $FiO_2$ value rises above or drops below the threshold value, so that flip-flop 16 ensures a stable behavior of the respiration system. An output signal 1 of flip-flop 16 causes control device 15 to cancel the adjustment on setting arrangement 19 for that period, while the original $FiO_2$ in storage 14 of the previous comparison period is maintained. If there is no rise above So or drop below Su after the expiration of an additional clock time, because patient 3 has again attained his original condition, control device 15 sets flip-flop 16 again on output signal 0. Control device 15 then adjusts the respiration parameter, whose adjustment was cancelled, in the direction opposite to the original adjustment. The cycle then repeats for the next parameter and time period. A patient will attain his original condition since the adjustments are small. FIG. 2 shows an embodiment with a warning device which is a safety feature if the conditions are not attained.

Returning to FIG. 1, control device 15 passes over or processes the next respiration parameter in like fashion until all the parameters have been treated. A new overall cycle then starts, each respiration parameter being adjusted in the direction in which it could contribute to a reduction of the $FiO_2$ value.

In this way parameter variations with an $FiO_2$ that is higher than before are automatically cancelled. Only parameter variations with an $FiO_2$ that is less than before are maintained and form with their $FiO_2$ a new upper threshold value. The $FiO_2$ is thus reduced to a minimum with constant $PaO_2$. The $FiO_2$ is reduced since, for any successful parameter adjustment, a new lower So value is obtained. The reduction in $FiO_2$, however, is only as permitted by regulator 5 which is controlled by the actual $PaO_2$ sensed at 4.

In the embodiment according to FIG. 2, sensors 20, 20' and 20" are connected to minimizer 12 for measuring additional patient data. Sensor 20 for the heart time minute volume (HZV) and the other sensor 20' for the arterial partial pressure of $CO_2$ ($PaCO_2$) are connected to patient 3. Sensor 20" for the breathing path pressure (P-air) is inserted into breathing gas line 2. The signals of sensors 20, 20' and 20" are transmitted to window comparators 21, 21' and 21", where upper and lower threshold values are given by threshold value transmitters (not shown). If the signal of the respective sensor 20, 20' and 20" is between these threshold values, the respective window comparator 21, 21' or 21" gives off a 0-signal. When the signal of the sensor leaves the range between the threshold values, window comparators 21, 21' or 21" give off a 1-signal and signals a warning on the respective connected warning devices 22, 22' and 22". The signals of window comparators 21, 21' and 21" and of minimizing comparator 13 are conducted parallel to OR-gate 23. Gate 23 gives off the output signal 0 when all inputs carry the signal 0, otherwise the output signal is 1. The OR-gate 23 is connected to flip-flop 16 of control device 15. Control device 15 is connected to setting arrangement 19, storage 14 and alarm device 24.

In addition, a $FiO_2$ window comparator 25 with connected warning device 26 is connected to the input of minimizing comparator 13, whose lower (Su) and upper (So) threshold values are set corresponding to the condition of patient 3 over threshold value transmitters (not shown). When the signal of mixer 7 leaves the range between these threshold values, the $FiO_2$ window comparator 25 signals a warning on warning device 26.

The sequence of operations is as described above. Upon the start of a first time period by master clock 18, control device 15 puts flip-flop 16 on output signal 0. At the same time it causes storage 14 to store the instantaneous $FiO_2$ of mixer 7 and to transmit it as So to minimizing comparator 13. Furthermore it causes, through setting arrangement 19, the adjustment of a first respiration parameter. If the $FiO_2$ value do not exceed the So or drop below the Su of minimizing comparator 13 and the actual values stay between the set values of the window comparators 21, during the first period, the output of OR-gate 23 remains on the 0-signal, and flip-flop 16 likewise remains on output signal 0. After the expiration of the first clock time period, the direction of the successful adjustment of the first respiration parameters is stored in control device 15. The above-described cycle then repeats itself, and a second respiration parameter is adjusted, whereby the $FiO_2$ just attained serves as a new threshold value So for minimizing comparator 13 during a second time period.

If an adjustment has the result, immediately or within the clock time period, that the value rises above the So or drops below the Su of minimizing comparator 13 or of a window comparator 21, 21' or 21", a 1-signal is formed at the output of OR-gate 23 which switches flip-flop 16 to output signal 1. Control device 15 thus causes cancellation of the adjustment, while the original $FiO_2$ remains in storage 14. If there is no further rise above the upper or drop below the lower threshold value after the expiration of an additional clock time, because patient 3 has regained his original condition, control device 15 puts flip-flop 16 again on output signal 0. Control device 15 then adjusts the respiration parameter whose adjustment was cancelled in the direction opposite to the original adjustment. The cycle then repeats itself.

If patient 3 should not regain his original condition after the unsuccessful adjustment has been cancelled, that is, if a 1-signal remains on the output of OR-gate 23, it must be assumed that a trend of the patient which is independent of the measures taken on the apparatus has led to a variation of these data. In this case, control device 15 shuts off the entire automatic system, and gives an optical and acoustical alarm over alarm device 24.

While specific embodiments of the invention have been shown and described in detail to illustrate the application of the principles of the invention, it will be understood that the invention may be embodied otherwise without departing from such principles.

What is claimed is:

1. A respiration system for minimizing inspiration breathing gas oxygen partial pressure $FiO_2$ while maintaining a desired arterial oxygen partial pressure $PaO_2$ for a patient, including a respirator which supplies breathing gas to the patient at a plurality of respirator parameters, comprising:

$PaO_2$ sensor means for sensing actual arterial oxygen partial pressure of a patient and supplying a signal corresponding thereto;

mixing means for mixing oxygen plus at least one other gas to supply a breathing gas mixture having an actual oxygen partial pressure $FiO_2$, value to the respirator, regulator means connected to said mixer for regulating the relative amounts of oxygen and the other gas in the breathing gas, said regulator means having a nominal $PaO_2$ value and receiving the $PaO_2$ sensor means signal for regulating the mixing means so that the actual $PaO_2$ value approaches the $PaO_2$ value;

comparator means connected to the mixing means and having a lower threshold value Su;

storage means connected to said mixing means and said comparator means for storing said actual $FiO_2$ value and supplying that value as the So value to said comparator means for a subsequent comparison step of said comparator means, said comparator means comparing said actual $FiO_2$ value from said mixing means with said Su and So values;

clocking means associated with said comparator means for establishing a time period as the duration of each comparison step;

parameter adjustment means connected to the respirator and the comparator means for selectively adjusting said plurality of respirator parameters, one at a time, in a selected direction and by a selected increment; and control means operatively connected to said comparator means and said storage means for controlling the parameter adjustment means to select one of said plurality of respiratory parameters and adjust said one selected respiratory parameter in accordance with one of the following conditions:

(i) with the actual $FiO_2$ value being between the Su and So values during a comparison step duration, the control means being operable to cause the parameter adjustment means to make an adjustment of said one parameter in a positive or negative direction, store the direction of said adjustment, and select another of said plurality of respiratory parameters for adjustment;

(ii) with the actual $FiO_2$ value being outside the range between the Su and So values, said control means being operable to maintain the So value of the previous comparison step in said storage means, reverse the direction of adjustment of the previous selected parameter and adjust the previous selected parameter by a selected increment in the reverse direction, and adjust the one selected parameter in a position or negative direction.

2. A respirator system according to claim 1, wherein said control means comprises a microprocessor for storing the direction of the adjustment of said parameter adjustment means.

3. A respirator system according to claim 2, including a plurality of additional sensor means for sensing additional conditions of the patient, a window comparator connected to each of said additional sensor means for producing a signal when a respective one of the conditions rises above and falls below selected values therefor, said former mentioned comparator means producing no signal when said actual $FiO_2$ value is between said So and Su values and for producing a signal when said actual $FiO_2$ value is outside the range between said So and Su values, an OR-gate having a plurality of inputs connected to each of said window comparators and said formerly mentioned comparator means and an output connected to said microprocessor, said microprocessor being operable to make adjustments in said respirator parameters through said parameter adjustment means with no signal coming from said OR-gate and, to cancel adjustment of one of of the respirator parameters and to change the direction of adjustment of said one of said respirator parameters with a signal coming from said OR-gate.

4. A respiration system according to claim 3 including a warning device connected to each of said window comparators.

5. A respiration system according to claim 3 including a warning device connected to said comparator means indicating when said comparator means continues to produce a signal even after said control means has changed the direction of said adjustment.

6. A respirator system according to claim 3 including an alarm connected to said control means.

7. A method of minimizing inspiration breathing gas oxygen partial pressure $FiO_2$ while maintaining a desired arterial oxygen partial pressure $PaO_2$ for a patient using a respirator which supplies breathing gas to the patient having a plurality of respirator parameters, comprising:
 (a) sensing the actual $PaO_2$ value of the patient;
 (b) providing a nominal $PaO_2$ value for the patient;
 (c) supplying the actual and nominal $PaO_2$ values to a regulator which is connected to a gas mixer, for controlling the gas mixer to adjust an amount of oxygen provided in breathing gas for the mixer to the patient so that the actual $PaO_2$ value can be made to approach the nominal $PaO_2$ value, the breathing gas having an actual oxygen partial pressure value $FiO_2$;
 (d) comparing the actual $FiO_2$ value with upper and lower threshold values for the $FiO_2$ value, So and Su, respectively;
 (e) storing the actual $FiO_2$ value to act as the So value in a following comparison step;
 (f) automatically selecting a parameter of the plurality of parameters and modifying said parameter in accordance with one of the following conditions:
  (i) with the actual $FiO_2$ value being between the stored So and the Su values, adjusting the selected parameter of the plurality of respirator parameters by a selected increment in a positive or negative direction, storing the direction of the adjustment, and repeating steps (a) to (f) for each respirator parameter;
  (ii) with the actual $FiO_2$ value being out of the range between So and Su, maintaining the So value of a previous comparison step, reversing the stored direction of the adjustment of the previous selected respirator parameter and adjusting the previous selected parameter by a selected increment in the reverse direction, and repeating steps (a) to (f) for the selected respirator parameter.

* * * * *